(12) United States Patent
Graf et al.

(10) Patent No.: US 11,727,559 B2
(45) Date of Patent: Aug. 15, 2023

(54) PNEUMOTHORAX DETECTION

(71) Applicant: Merative US L.P., Ann Arbor, MI (US)

(72) Inventors: Benedikt Graf, Charlestown, MA (US); Yiting Xie, Cambridge, MA (US); Arkadiusz Sitek, Ashland, MA (US); Amin Katouzian, Lexington, MA (US)

(*) Notice: Subject to any disclaimer, the term of this patent is extended or adjusted under 35 U.S.C. 154(b) by 420 days.

(21) Appl. No.: 16/918,067

(22) Filed: Jul. 1, 2020

(65) Prior Publication Data

US 2022/0005185 A1  Jan. 6, 2022

(51) Int. Cl.
*G06T 7/00* (2017.01)
*G16H 50/30* (2018.01)
(Continued)

(52) U.S. Cl.
CPC .......... *G06T 7/0012* (2013.01); *A61B 5/7267* (2013.01); *A61B 6/12* (2013.01); *A61B 6/5217* (2013.01); *G06N 20/00* (2019.01); *G06T 1/20* (2013.01); *G06T 7/11* (2017.01); *G06T 7/70* (2017.01); *G16H 30/40* (2018.01); *G16H 50/20* (2018.01); *G16H 50/30* (2018.01); *G06T 2207/10116* (2013.01); *G06T 2207/20081* (2013.01); *G06T 2207/30061* (2013.01)

(58) Field of Classification Search
CPC . G06T 1/20; G06T 7/0012; G06T 7/11; G06T 7/70; G06T 2207/10081; G06T 2207/10088; G06T 2207/10116; G06T 2207/20081; G06T 2207/20084; G06T 2207/30061; A61B 5/7267; A61B 6/12; A61B 6/5217; A61B 6/50; G06N 3/08; G06N 5/02; G06N 20/00; G16H 30/40; G16H 50/20; G16H 50/30; G16H 50/70
See application file for complete search history.

(56) References Cited

U.S. PATENT DOCUMENTS 5,668,888 A    9/1997 Doi
6,650,924 B2  11/2003 Kuth
(Continued)

FOREIGN PATENT DOCUMENTS

CN    108596198 A    9/2018
CN    109741823 A    5/2019
(Continued)

OTHER PUBLICATIONS

Baltruschat, et al., "Comparison of Deep Learning Approaches for Multi-Label Chest X-Ray Classification." Scientific Reports, vol. 9, No. 6381, https://doi.org/10.1038/s41598-019-42294-8, Apr. 23, 2019, pp. 1-10.
(Continued)

*Primary Examiner* — Nay A Maung
*Assistant Examiner* — Jose M Torres
(74) *Attorney, Agent, or Firm* — Stephen J. Walder, Jr.

(57) ABSTRACT

A computer implemented method, a data processing system and a computer program product to determine a likelihood of pneumothorax of a patient, the method including assessing a digital image of a chest x-ray of the patient, applying a standard detection pipeline to the digital image, applying a confounding factor detector to the digital image, and applying a high-resolution detection pipeline to the digital image.

20 Claims, 5 Drawing Sheets

(51) Int. Cl.
*G16H 30/40* (2018.01)
*G16H 50/20* (2018.01)
*G06N 20/00* (2019.01)
*G06T 1/20* (2006.01)
*G06T 7/11* (2017.01)
*A61B 6/00* (2006.01)
*A61B 5/00* (2006.01)
*A61B 6/12* (2006.01)
*G06T 7/70* (2017.01)

(56) References Cited

U.S. PATENT DOCUMENTS

| | | | |
|---|---|---|---|
| 8,103,077 B2 | 1/2012 | Hong | |
| 2012/0263366 A1* | 10/2012 | Huo | G06T 5/009 382/132 |
| 2018/0047158 A1* | 2/2018 | Geva | G16H 50/30 |
| 2018/0137244 A1* | 5/2018 | Sorenson | G16H 30/20 |
| 2019/0150857 A1* | 5/2019 | Nye | A61B 6/037 |
| 2019/0156484 A1 | 5/2019 | Nye | |
| 2019/0340752 A1* | 11/2019 | Brestel | G06V 10/764 |
| 2021/0005307 A1* | 1/2021 | Knoplioch | G16H 10/60 |
| 2021/0059627 A1* | 3/2021 | Kim | G16H 50/20 |
| 2021/0192727 A1* | 6/2021 | Ward | G06V 10/82 |
| 2021/0312629 A1* | 10/2021 | Cheng | G16H 30/40 |
| 2021/0383536 A1* | 12/2021 | Schudlo | G16H 50/20 |

FOREIGN PATENT DOCUMENTS

| | | | | |
|---|---|---|---|---|
| WO | WO-2018013703 A1 * | 1/2018 | | A61B 5/08 |
| WO | WO-2021248187 A1 * | 12/2021 | | |

OTHER PUBLICATIONS

Chan, et al., "Effective Pneumothorax Detection for Chest X-Ray Images Using Local Binary Pattern and Support Vector Machine," Hindawi Journal of Healthcare Engineering, vol. 2018, Article ID 2908517, https://doi.org/10.1155/2018/2908517, Apr. 3, 2018, pp. 1-11.

Dietsche, "Zebra Medical Vision lands FDA approval for AI pneumothorax alert product", The product, HelathPNX, automatically flags findings of suggestive of pneumothorax based on chest X-rays or digital radiography scans and informs the medical team, Accessed on Apr. 17, 2020, 8 pages.

FDA U.S. Food & Drug Administration, "Re: K190362", May 6, 2019, https://www.accessdata.fda.gov/cdrh_docs/pdf19/K190362.pdf, , 8 pages.

FDA, "510(k) Premarket Notification", https://www.accessdata.fda.gov/scrlpts/cdrh/cfdocs/cfpmn/pmn.cfm?ID=K183182, Accessed on Apr. 17, 2020, 3 pages.

Gooβen, et al., "Deep Learning for Pneumothorax Detection and Localization in Chest Radiographs", https://arxiv.org/abs/1907.07324, Jul. 16, 2019, pp. 1-9.

Grace Period Disclosure, IBM Watson Health, "IBM Watson Imaging Clinical Review 3.1", Release Notes, © Copyright IBM Corporation. 2019, 2020, 13 pages.

http://newsroom.gehealthcare.com/ai-embedded-x-ray-system-could-help-speed-up-detection-of-a-collapsed-lung/, "AI-embedded X-Ray system could help speed up detection of a collapsed lung", Nov. 27, 2018, Article, GE Healthcare, 8 pages.

Jun, et al., "Automated diagnosis of pneumothorax using an ensemble of convolutional neural networks with multi-sized chest radiography images", https://arxiv.org/abs/1804.06821, Apr. 18, 2018, pp. 1-18.

Mell et al., "The NIST Definition of Cloud Computing", Recommendations of the National Institute of Standards and Technology, Special Publication 800-145, Sep. 2011, 7 pages.

Sze-To, et al., "tCheXNet: Detecting Pneumothorax on Chest X-Ray Images Using Deep Transfer Learning", https:/doi.org/10.1007/978-3-030-27272-2_28, 2019, pp. 325-332.

Taylor, et al., "Automated detection of moderate and large pneumothorax on frontal chest X-rays using deep convolutional neural networks: A retrospective study", PLOS Medicine 15(11): e1002697, https://doi.org/10.1371/journal.pmed.1002697, Nov. 20, 2018, pp. 1-15.

* cited by examiner

PNEUMOTHORAX DETECTION

STATEMENT REGARDING PRIOR DISCLOSURES BY THE INVENTOR OR A JOINT INVENTOR

Aspects of the present invention may have been disclosed by the inventor, or a joint inventor, in the IBM Watson Imaging Clinical Review 3.1 Release Notes, made available to the public on May 12, 2020. These aspects, as they may appear in the claims, may be subject to consideration under 35 U.S.C. § 102(b)(1)(A).

BACKGROUND

The present invention relates to image processing, and more specifically to a computer implemented method, data processing system and computer program product for machine learning to analyze an image for a medical diagnosis.

Pneumothorax is a serious medical condition consisting of air leakage into the pleural space of a chest cavity between a lung and a wall of the chest and is also known as a collapsed lung. A chest x-ray is a common diagnostic image used for diagnosis of pneumothorax. Pneumothoraces can be a very subtle finding and can potentially be missed when analyzing the diagnostic image. Artificial Intelligence algorithms can assist in the interpretation of chest x-ray images for the detection of pneumothorax and can benefit patient diagnosis to help improve patient treatment and outcome.

SUMMARY

According to a first aspect of the present invention, there is provided a computer implemented method, a data processing system and a computer program product to determine a likelihood of pneumothorax of a patient, the method including assessing a digital image of a chest x-ray of the patient, applying a standard detection pipeline to the digital image, applying a confounding factor detector to the digital image, and applying a high-resolution detection pipeline to the digital image.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Various types of machine learning models may be built to create predictive results for various domains, such as retail, social media content, business, technology, medical, academic, government, industrial, food chain, legal or automotive. Machine learning models may also include deep learning models and artificial intelligence. Training and updating a machine learning model may include supervised, unsupervised and semi-supervised machine learning procedures. Supervised learning may use a labeled dataset or a labeled training set to build, train and update a model. Unsupervised learning may use all unlabeled data to train a deep learning model. Semi-supervised learning may use both labeled datasets and unlabeled datasets to train a deep learning model. The present invention is composed of many individual machine learning models. These models can be trained using supervised, unsupervised or semi-supervised learning.

Supervised learning and semi-supervised learning may incorporate ground truth by having an individual check the accuracy of the data, data labels and data classifications. Individuals are typically a subject matter expert who have extensive knowledge in the particular domain of the dataset. The subject matter expert input may represent ground truth for the machine learning model and the provided ground truth may raise the accuracy of the model. The subject matter expert may correct, amend, update or remove the classification of the data or data labels by manually updating the labeled dataset. Machine learning models improve in accuracy as datasets are corrected by a subject matter expert, however, manually annotating large amounts of data may be time-intensive and complex.

According to an embodiment, supervised or semi-supervised machine learning may be used to allow an individual (e.g., a user, a subject matter expert, an expert or an administrator) to have some control over the machine learning model by having the ability to validate, alter, update or change the training set. Users may provide input or feedback into a machine learning model by altering the training set as opposed to an unsupervised machine learning environment, when a user may not provide input to the data. The training set of data may include parameters of a classifier or a label for learning purposes and a supervised or semi-supervised machine learning environment may allow user to update the training set based on user experience.

Various cognitive analyses may be used, such as natural language processing, semantic analysis and sentiment analysis during the building and training of a machine learning model. The present invention does not directly make use of these types of cognitive analysis. However, as the present invention is composed of machine learning algorithms, cognitive analysis may be used to create the machine learning models. All models used in the invention are trained separately and then combined to create the invention. The cognitive analytics may analyze both structured and unstructured data to be incorporated into the machine learning process. Natural language processing may be used to analyze the quality of data, feedback or a conversation based on the received data. Structured data may include data that is highly organized, such as a spreadsheet, relational database or data that is stored in a fixed field. Unstructured data may include data that is not organized and has an unconventional internal structure, such as a portable document format (PDF), an image, a presentation, a webpage, video content, audio content, an email, a word processing document or multimedia content. The received data may be processed through natural language processing to extract information that is meaningful to a user.

Historical data and current data may be used for analysis and added to a corpus or a database that stores the training data, the real-time data, the predictive results, the user feedback and the model performance. Current data may, for example, be received from an internet of things (IoT) device, a global positioning system (GPS), a sensor, a smart watch, a smart phone, a smart tablet, a personal computer or an automotive device. Current data may generally refer to, for example, data relating to a user's preference and a collection method to obtain the user's preferences, such as via typewritten messages, video content, audio content or biometric content. Historical data may include, for example, training data, user preferences, user historical feedback, previous model performance, model performance levels for each user and model learning curves.

As previously described, pneumothorax is a serious medical condition consisting of air leakage into the pleural space of a chest cavity between a lung and a wall of the chest and is also known as a collapsed lung. A chest x-ray is a common imaging exam for diagnosis of a pneumothorax. Pneumothoraces can be very subtle and can potentially be missed when reading the x-ray. Artificial Intelligence algorithms can assist in the interpretation of chest x-ray images for the detection of a pneumothorax and can benefit patient diagnosis to help improve patient treatment and outcome.

Embodiments of the present invention relate to the field of computing, and more particularly to image processing. The following exemplary embodiments provide a system, method, and program product to, among other things, use machine learning to analyze an image for automated detection of a pneumothorax on a chest x-ray. The design of the system incorporates many components to be considered in the assessment of the chest x-ray for diagnosing pneumothorax. The system considers technical factors such as image quality and patient positioning, various ways in which pneumothorax can appear on the x-ray as well as other conditions that can mimic pneumothorax. Therefore, the present embodiment has the capacity to improve the technical field of image processing for detection of pneumothorax using an image assessment, a standard detection pipeline, a confounding factor detection and a high-resolution detection pipeline.

Figure 1:
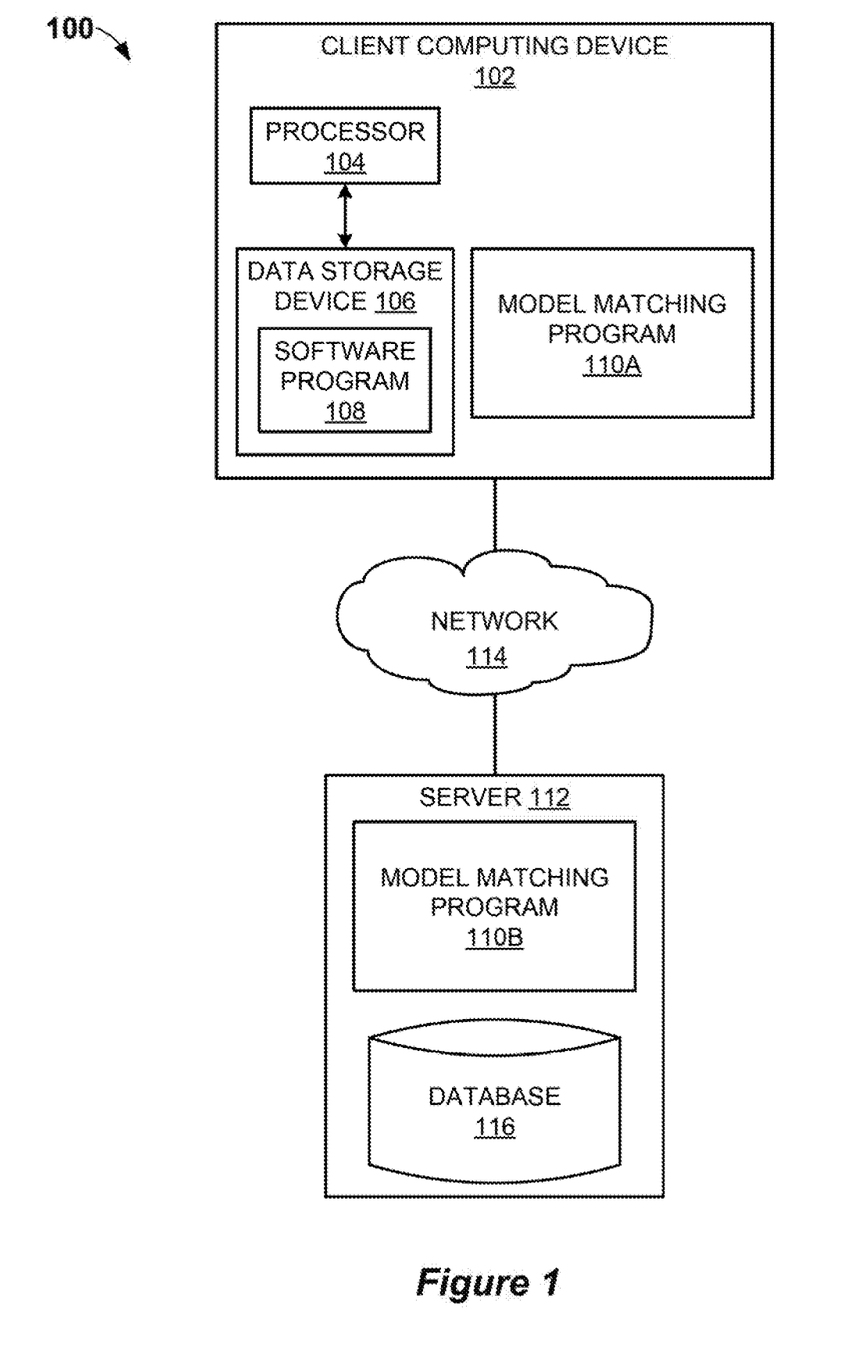
FIG. 1 depicts an exemplary networked computer environment according to an embodiment.

Referring to FIG. 1, an exemplary networked computer environment 100 is depicted, according to an embodiment. The networked computer environment 100 may include client computing device 102 and a server 112 interconnected via a communication network 114. According to at least one implementation, the networked computer environment 100 may include a plurality of client computing devices 102 and servers 112, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a software program 108 and a pneumothorax detection program 110A and communicate with the server 112 via the communication network 114, in accordance with an embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 3, the client computing device 102 may include internal components and external components, respectively.

The server 112 may be a laptop computer, netbook computer, personal computer (PC), a desktop computer, or any programmable electronic device or any network of programmable electronic devices capable of hosting and running a pneumothorax detection program 110B and a database 116 and communicating with the client computing device 102 via the communication network 114, in accordance with embodiments of the invention. As will be discussed with reference to FIG. 3, the server 112 may include internal components and external components, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

According to the present embodiment, the pneumothorax detection program 110A, 110B may be a program capable of identifying pneumothorax of a patient by reviewing diagnostic images, such as an x-ray, a CT or computed tomography scan, or a magnetic resonance image, otherwise known as an MIll. The pneumothorax detection method is explained in further detail below with respect to FIG. 2.

Figure 2:
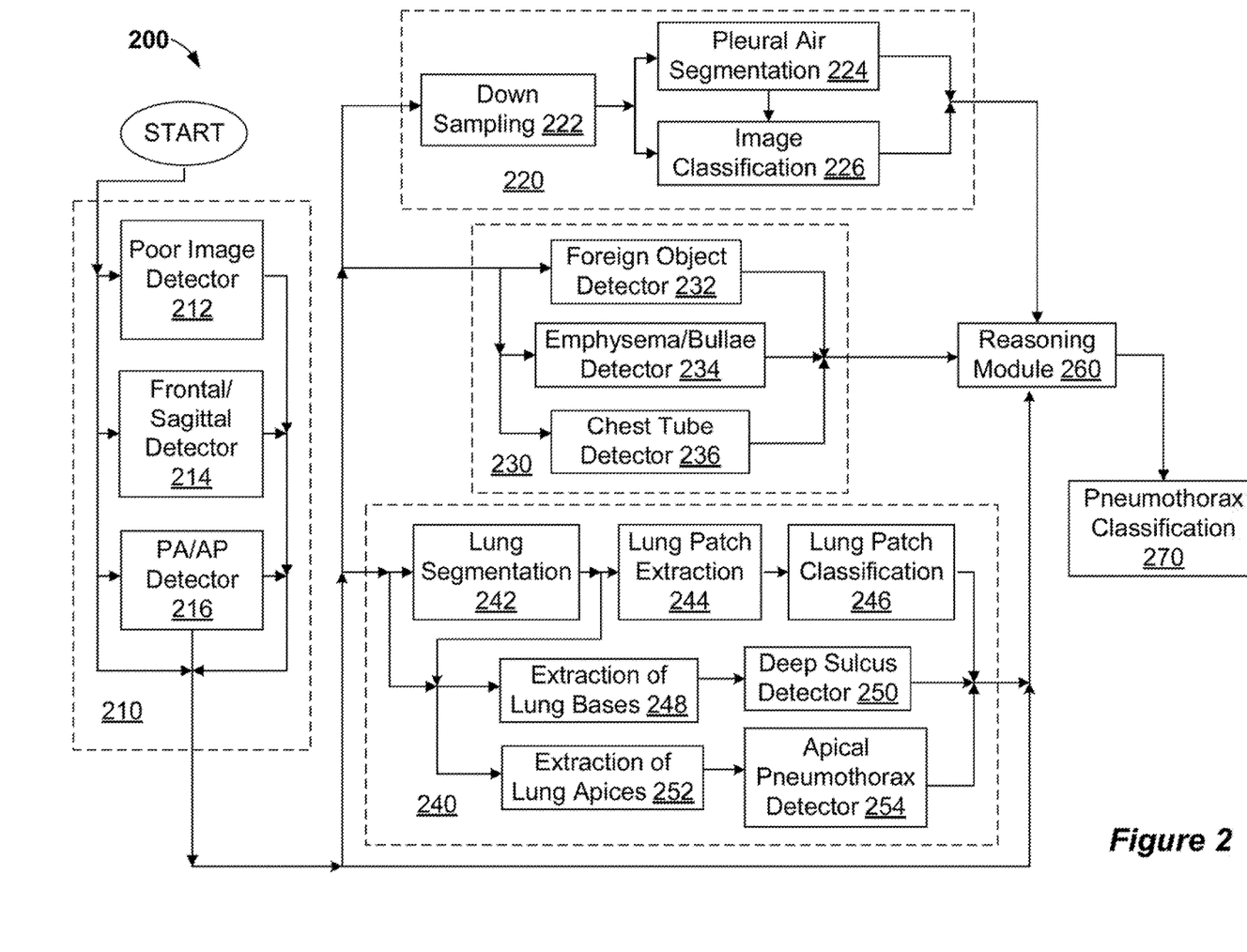
FIG. 2 depicts an operational flowchart illustrating a diagnosis process according to an embodiment.

Referring now to FIG. 2, an operational flowchart illustrating a diagnosis process 200 is depicted according to an embodiment. The diagnosis process 200 may include image assessment 210, standard detection pipeline 220, confounding factor detection 230, high-resolution detection pipeline 240, reasoning module 260 and pneumothorax classification 270.

The image assessment 210 may include a poor image detector 212, a front/sagittal detector 214, and a posteroanterior or anteroposterior (hereinafter "PA/AP") detector 216. Input to the image assessment 210 includes a chest x-ray, or other diagnostic image. The image assessment 210 evaluates the chest x-ray for various technical factors that are used in other sections of the diagnosis process 200 and in the diagnosis of pneumothorax. The diagnostic images as input to the image assessment 210 are available as input to the poor image detector 212, to the frontal/sagittal detector 214 and to the PA/AP detector 216. Each of the poor image detector 212, the frontal/sagittal detector 214 and the PA/AP detector 216 can be an individual neural network for machine learning.

The poor image detector 212 assesses the diagnosis images for factors that may indicate that the image quality is insufficient for further processing. This can include poor patient positioning, over or under exposure, etc. The poor image detector can be a machine learning model that has been trained based on a set of example images that have been categorized as acceptable or poor quality by an expert such as a radiologist.

The front/sagittal detector 214 classifies the image as either a frontal or a sagittal view. A frontal view divides the body into front and back halves. A sagittal view divides the body into left and right halves. Typically, only a frontal chest x-ray is considered for evaluation of pneumothorax. The frontal/sagittal detector can be a machine learning model that has been trained on a set of example images that have been categorized as frontal or sagittal by an expert such as a radiologist.

The PA/AP detector 216 further classifies a frontal image as either PA or AP. This is an important differentiation step, as a posteroanterior or PA diagnostic image is an image taken on a patient that is in the supine position. Alternatively, an anteroposterior or AP diagnostic image is taken on a patient who is standing. The location of air accumulation in the chest depends on patient position. Therefore, the subsequent pneumothorax detection pipeline can focus on a specific anatomical region which is more likely to contain pleural air. Specifically, a patient in an erect or standing position who has an AP diagnostic image taken, may have air accumulation in apicolateral pleural space, surrounding an upper portion of a lung when they have pneumothorax. Alternatively, a patient in a supine position who has a PA diagnostic image taken, may have air accumulation in the anteromedial pleural space, surrounding a lower portion or base of the lung, when they have pneumothorax. The AP/PA detector can be a machine learning model that has been trained on a set of example images that have been categorized as AP or PA by an expert such as a radiologist.

The image assessment 210 output may include the original diagnostic image, output from the poor image detector 212, output classification from the frontal/sagittal detector 214 and output classification from the PA/AP detector 216. The image assessment 210 output may feed into the standard detection pipeline 220, the confounding factor detection 230 and the high-resolution detection pipeline 240. The image assessment 210 output may feed into the reasoning module 260.

The standard detection pipeline 220 may include down sampling 222, pleural air segmentation 224 and image classification 226. Output from the image assessment 210, including for example the frontal/sagittal detector 214, may be an input to the down sampling 222 of the standard detection pipeline 220. Output from the down sampling 222 may be input to both the pleural air segmentation 224 and to the image classification 226. Output from the pleural air segmentation 224 may input to the image classification 226. Each of the pleural air segmentation 224 and the image classification 226 could be an individual neural network for machine learning.

The standard detection pipeline 220 may be referred to as a primary detection pipeline. The standard detection pipeline 220 is a main pipeline for detecting pneumothorax and consists of evaluating individual images at an intermediate resolution.

The down sampling 222 reduces an amount of data from the image for further processing by the pleural air segmentation 224 and the image classification 226. Typical algorithms for evaluating full images do not work well on a full resolution diagnostic images and thus some down sampling is required. Full resolution images do not work well because they require much larger algorithms which are more difficult to train and require more training data which can be difficult and expensive to obtain. For example, an image of 2000 to 3000 pixels may be reduced to 500 to 1000 pixels by the down sampling 222.

The pleural air segmentation 224 is a segmentation model that identifies a region of pleural air from the down sampling 222 of the images. The pleural air segmentation model can be a machine learning model that has been trained on a set of example images that have been manually annotated by an expert such as a radiologist.

The image classification 226 model takes as an input the original image as well as the results of the pleural air segmentation 224 and generates a probability of the image containing pneumothorax. This classification model can be a deep learning model that has been trained on a set of example images that have been manually categorized by an expert such as a radiologist. Certain types of classification models are designed to produce a probability value between 0 and 1, with 0 identifying a low probability or no probability, and 1 identifying a very high probability.

Output from the standard detection pipeline 220, including output from the pleural air segmentation 224 and from the image classification 226 may be input to the reasoning module 260.

The confounding factor detection 230 includes a foreign object detector 232, an emphysema/bullae detector 234 and a chest tube detector 236. Output from the image assessment 210, for example the frontal/sagittal detector 214, may be an input to the confounding factor detection 230. Output from the image assessment 210 may be input to the foreign object detector 232, to the emphysema/bullae detector 234 and to the chest tube detector 236. Output from the confounding factor detection 230 may input to the reasoning module 260, including output from the foreign object detector 232, output from the emphysema/bullae detector 234 and output from the chest tube detector 236. Each of the foreign object detector 232, emphysema/bullae detector 234 and the chest tube detector 236 may be an individual neural network for machine learning.

The confounding factor detection 230 identifies specific conditions and features that can improve assessment of pneumothorax on chest x-rays. The confounding factor detection 230 performs detection of these features so they can be used by the final reasoning module 260.

The foreign object detector 232 can help to identify certain features which may cause a shadow on an x-ray that can mimic features of a pneumothorax. Common examples of this include shadows from a breast in a patient with breast tissue, and foreign objects such as clothing or defibrillator paddles. Specific detection of these types of features can reduce false positives. The foreign object detector can be a machine learning model that has been trained on a set of example images that have been categorized by an expert such as a radiologist.

The emphysema/bullae detector 234 can help reduce false positives. Emphysema and bullous disease can result in air cavities inside the lungs. These air pockets can mimic the features of pneumothorax. Emphysema is a condition in which air sacs of the lungs are damaged and enlarged. Bullous disease is a rare skin condition that causes large, fluid-filled blisters called bullae on skin. Identifying factors for additional illnesses and conditions may be included in the emphysema/bullae detector 234. The emphysema/bullae detector can be a machine learning model that has been trained on a set of example images that have been categorized by an expert such as a radiologist.

The chest tube detector 236 can help identify pneumothorax by identifying a chest tube on the image. A chest tube is a plastic tube inserted into a lung to evacuate air from the pleural space in order to treat pneumothorax. Identification of a chest tube in the image can assist in the overall reasoning for a positive detection and assessment of pneumothorax. The chest tube detector can be a machine learning model that has been trained on a set of example images that have been categorized by an expert such as a radiologist.

The high-resolution detection pipeline 240 includes lung segmentation 242, lung patch extraction 244, lung patch classification 246, extraction of lung base 248, a deep sulcus detector 250, an extraction of lung apices 252 and an apical pneumothorax detector 254. Output from the image assessment 210, for example the PA/AP detector 216, may be an input to the high-resolution detection pipeline 240. Input into the high-resolution detection pipeline 240 may be input to the lung segmentation 242, to the extraction of lung bases 248 and to the extraction of lung apices 252. Output from the lung segmentation 242 may input to the lung patch extraction 244 and to the extraction of lung bases 248 and to the extraction of lung apices 252. Output from the lung patch extraction 244 may be input to the lung patch classification 246. Output from the extraction of lung bases 248 may be input to the deep sulcus detector 250. Output from the extraction of lung apices 252 may be input to the apical pneumothorax detector 254. Output from the high-resolution detection pipeline 240 may input to the reasoning module 260, including output from the lung patch classification 246, output from the deep sulcus detector 250 and output from the apical pneumothorax detector 254. Each of the lung segmentation 242, lung patch classification 246, deep sulcus detector 250 and the apical pneumothorax detector 254 can be an individual neural network for machine learning.

The high-resolution detection pipeline 240 increases an accuracy of detecting subtle pneumothoraces by extracting high resolution patches from areas of the lung which are more likely to contain accumulated pleural air. For example, depending on whether the study is an AP or PA film, as determined by the output of the PA/AP detector 216, a different region or patch of the digital image corresponding to a different region of a lung, would be extracted.

The lung segmentation 242 is a segmentation model that identifies different regions of the chest on a frontal x-ray image, in order to determine which regions can be examined more closely for identification of pneumothorax. The lung segmentation model can be a machine learning model that has been trained on a set of example images that have been manually annotated by an expert such as a radiologist.

The lung patch extraction 244 is an extraction of a high-resolution patch, or data section, from the original digital image, as identified in the lung segmentation 242. The lung patch extraction 244 may extract one or more patches of data, each corresponding to a different region of the lung. The lung patch extraction is based on standard image processing that consists of simply extracting a smaller portion of the original image.

The lung patch classification 246 identifies a specific region of the lung which corresponds to each of the patches of the one or more patches of data. The lung patch classification performs a detection of any type of pneumothorax on the lung patch image that was extracted in 244. Whereas the deep sulcus detector 250 and the apical pneumothorax detector 254 specifically detect one type of pneumothorax, this classifier is general enough to detect both types. The lung patch classification can be a machine learning model that has been trained on a set of example images that have been categorized by an expert such as a radiologist.

The extraction of lung bases 248 uses the output from the lung segmentation 242 to extract the portion of the image or data which correspond to a lung base. AP frontal images are typically taken when the patient is lying down. In a patient with pneumothorax this results in the accumulation of air in the base of a lung. The lung base extraction is based on standard image processing that consists of simply extracting a smaller portion of the original image.

The deep sulcus detector 250 uses the high-resolution patch of the lung base from the extraction of lung bases 248 to process and classify whether a deep sulcus pneumothorax is present. On a chest x-ray, deep sulcus is a subtle finding and may be difficult to diagnose. In order to detect this type of pnuemothoraces, the high-resolution patch of the lung base is closely examined, and a determination is made whether deep sulcus is detected. The deep sulcus detector can be a machine learning model that has been trained on a set of example images that have been categorized by an expert such as a radiologist.

The extraction of lung apices 252 uses the output from lung segmentation 242 to extract the portion of the image or data which correspond to a lung apex. PA frontal images are typically taken when the patient is standing. In a patient with pneumothorax this results in the accumulation of air in the apices (tips) of the lungs. The lung apex extraction is based on standard image processing that consists of simply extracting a smaller portion of the original image.

To increase the accuracy of detecting small apical pnuemothoraces, high resolution patches are extracted from the original image from the region of the lung apices.

The apical pneumothorax detector 254 uses the high-resolution patch of the lung apices from the lung patch classification 246 and process this to classify whether an apical pneumothorax is present at the tip of the lung. The apical pneumothorax detector can be a machine learning model that has been trained on a set of example images that have been categorized by an expert such as a radiologist.

The examination of specific regions of the lung help to increase a likelihood of accurately diagnosing pnuemothoraces by specifically looking in different regions of the lung for indications of presence of air in the lung sac, by focusing on a small area with a high-resolution of data for more accurate diagnosis.

The reasoning module 260 has input from the original x-ray, from the image assessment 210, from the standard detection pipeline 220, from the confounding factor detection 230, and from the high-resolution detection pipeline 240. The reasoning module 260 may be an individual neural network for machine learning. The reasoning module 260 utilizes the inputs to make a diagnosis of whether pneumothorax is present in a lung of the patient. The reasoning module can be implemented in various ways. In one implementation it can be a set of rules that take the inputs and make a decision using simple thresholds and comparisons. In another implementation it can be a machine learning model that is trained based on a set of examples created by experts such as radiologists.

Positive output from the poor image detector, from the foreign object detector 232 and from the emphysema/bullae detector 234 may lower a likelihood of a positive pneumothorax diagnosis from the reasoning module 260, due to a situation where an image on an x-ray may appear to have common characteristics as pneumothorax but there may be an alternate explanation. An output from the PA/AP detector 216 indicating the patient is in a supine or AP position, in combination with a positive output from the apical pneumothorax detector 254 may lower a likelihood of a positive pneumothorax diagnosis, due to a patient laying down would not likely have air in their air sack along an apex of their lung. An output from the PA/AP detector 216 indicating the patient is in an erect or PA position, in combination with a positive output from the deep sulcus detector 250 may lower a likelihood of a positive pneumothorax diagnosis, due to a patient standing would not likely have air in their air sack along a base of their lung.

Positive output from the chest tube detector 236 may increase a likelihood of a positive pneumothorax diagnosis from the reasoning module 260, due to a patient with a chest tube may be more likely to have pneumothorax. An output from the PA/AP detector 216 indicating the patient is in a supine or AP position, in combination with a positive output from the deep sulcus detector 250 may increase a likelihood of a positive pneumothorax diagnosis, due to a patient laying down with pneumothorax is more likely have air in their air sack along an apex of their lung. An output from the PA/AP detector 216 indicating the patient is in an erect or PA position, in combination with a positive output from the apical pneumothorax detector 254 may increase a likelihood of a positive pneumothorax diagnosis, due to a patient standing with pneumothorax would likely have air in their air sack along a base of their lung.

The reasoning module 260 may output to the pneumothorax classification 270. The reasoning module 260 combines the information from all the different detection pathways which are input to the reasoning module 260 to make final determination about whether a pneumothorax is present is the image. The reasoning module 260 can make logical conclusions based on the inputs. For example if the result from the deep sulcus detector 250 indicates the presence of a pneumothorax but the AP/PA classification algorithm indicates the study is a PA examination where the patient is standing, the reasoning module 260 can conclude that the deep sulcus detector 250 likely is providing a false detection because patients that are standing very rarely would have a deep sulcus. Deep sulcus would generally be diagnosed only in a patient in a prone position.

The pneumothorax classification 270 may be an individual neural network for machine learning. The pneumothorax classification 270 utilizes the input from the reasoning module 260 to further classify pneumothorax. Pneumothorax may be classified into spontaneous or traumatic. Spontaneous pneumothorax can further be classified as primary, which means the patient has no underlying lung disease, or as secondary, where the patient has an underlying lung disease. Traumatic pneumothorax may be further classified as open or closed, meaning with or without chest wall damage respectively. Spontaneous pneumothorax and traumatic pneumothorax may be further classified as a tension pneumothorax if air surrounding the lung increases in pressure, which would require emergency medical treatment.

It may be appreciated that FIG. 2 provides only an illustration of an implementation and does not imply any limitations with regard to how different embodiments may be implemented. Many modifications to the depicted environments may be made based on design and implementation requirements.

Figure 3:
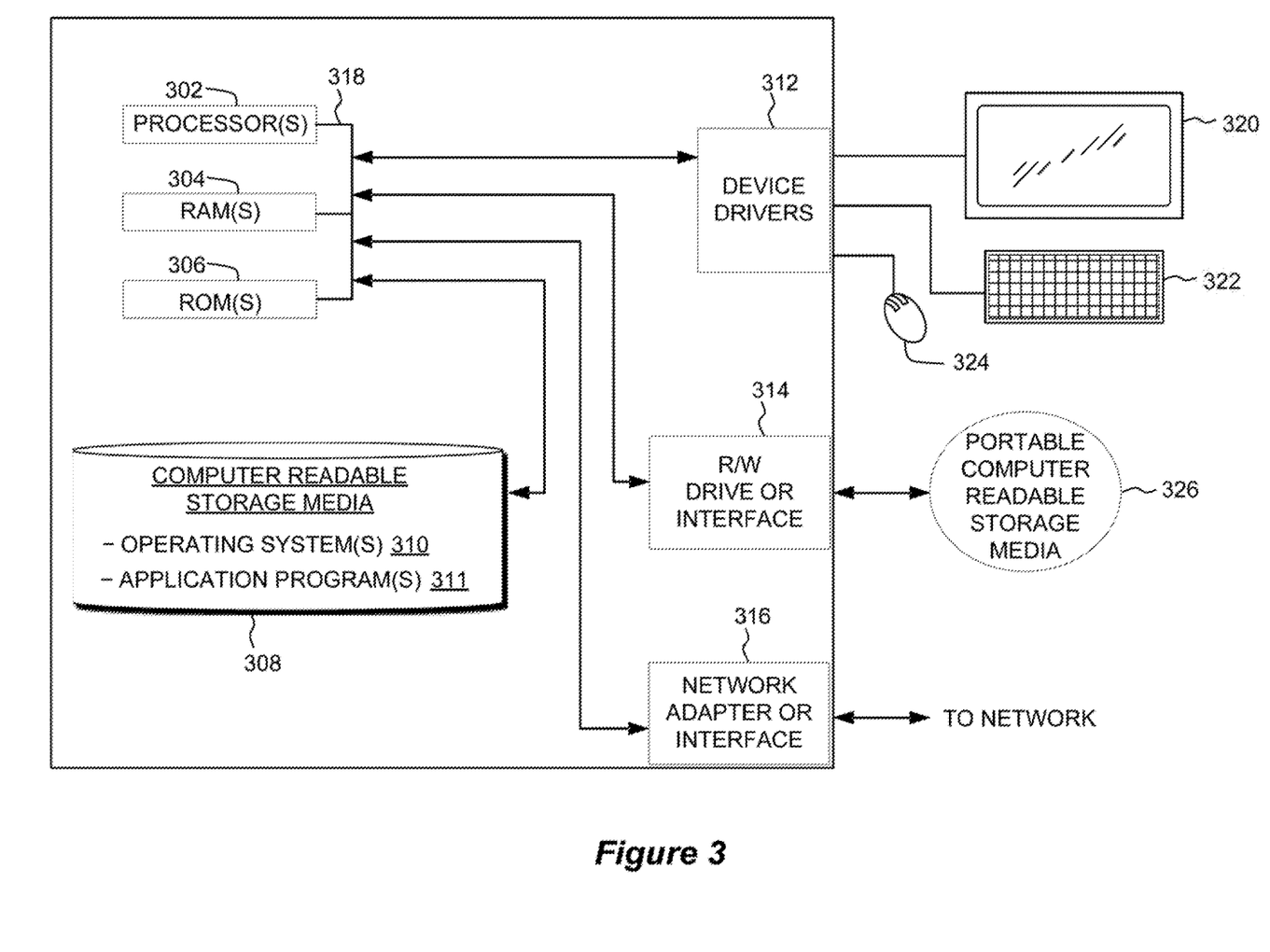
FIG. 3 depicts a block diagram of internal and external components of computers and servers depicted in FIG. 1 according to an embodiment.

Referring now to FIG. 3, a block diagram of components of a computing device, such as the server 112 of FIG. 1, in accordance with an embodiment of the present invention is shown. It should be appreciated that FIG. 3 provides only an illustration of an implementation and does not imply any limitations with regard to the environments in which different embodiments may be implemented. Many modifications to the depicted environment may be made.

The computing device may include one or more processors 302, one or more computer-readable RAMs 304, one or more computer-readable ROMs 306, one or more computer readable storage media 308, device drivers 312, read/write drive or interface 314, network adapter or interface 316, all interconnected over a communications fabric 318. Communications fabric 318 may be implemented with any architecture designed for passing data and/or control information between processors (such as microprocessors, communications and network processors, etc.), system memory, peripheral devices, and any other hardware components within a system.

One or more operating systems 310, and one or more application programs 311 are stored on one or more of the computer readable storage media 308 for execution by one or more of the processors 302 via one or more of the respective RAMs 304 (which typically include cache memory). For example, the diagnosis process 200, may be stored on the one or more of the computer readable storage media 308. In the illustrated embodiment, each of the computer readable storage media 308 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

The computing device may also include the R/W drive or interface 314 to read from and write to one or more portable computer readable storage media 326. Application programs 311 on the computing device may be stored on one or more of the portable computer readable storage media 326, read via the respective R/W drive or interface 314 and loaded into the respective computer readable storage media 308.

The computing device may also include the network adapter or interface 316, such as a TCP/IP adapter card or wireless communication adapter (such as a 4G wireless communication adapter using OFDMA technology). Application programs 311 may be downloaded to the computing device from an external computer or external storage device via a network (for example, the Internet, a local area network or other wide area network or wireless network) and network adapter or interface 316. From the network adapter or interface 316, the programs may be loaded onto computer readable storage media 308. The network may comprise copper wires, optical fibers, wireless transmission, routers, firewalls, switches, gateway computers and/or edge servers.

The computing device may also include a display screen 320, a keyboard or keypad 322, and a computer mouse or touchpad 324. Device drivers 312 interface to display screen 320 for imaging, to keyboard or keypad 322, to computer mouse or touchpad 324, and/or to display screen 320 for pressure sensing of alphanumeric character entry and user selections. The device drivers 312, R/W drive or interface 314 and network adapter or interface 316 may comprise hardware and software (stored on computer readable storage media 308 and/or ROM 306).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access a normalized search engine or related data available in the cloud. For example, the normalized search engine could execute on a computing system in the cloud and execute normalized searches. In such a case, the normalized search engine could normalize a corpus of information and store an index of the normalizations at a storage location in the cloud. Doing so allows a user to access this information from any computing system attached to a network connected to the cloud (e.g., the Internet).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
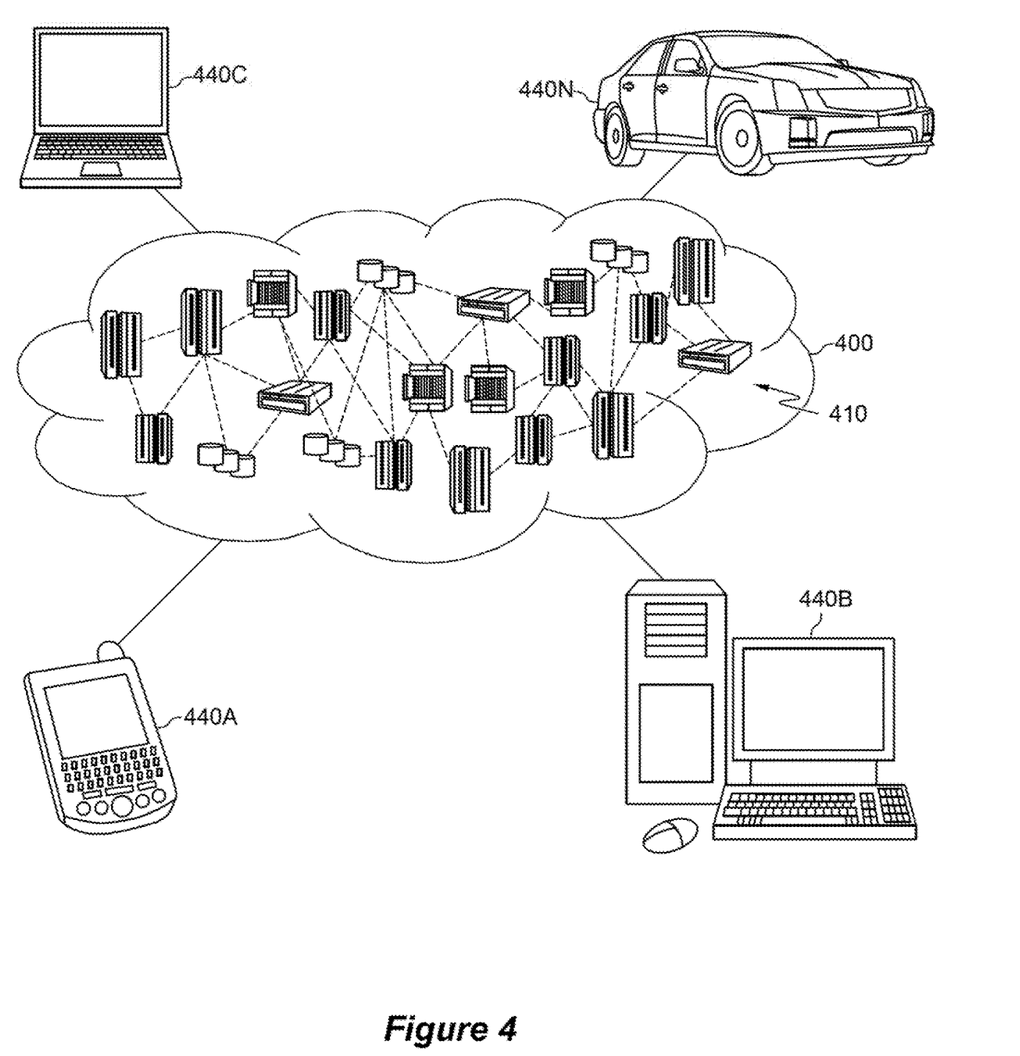
FIG. 4 depicts a cloud computing environment according to an embodiment of the present invention.

Referring now to FIG. 4, illustrative cloud computing environment 400 is depicted. As shown, cloud computing environment 400 includes one or more cloud computing nodes 410 with which local computing devices used by cloud consumers, such as, for example, personal digital assistant (PDA) or cellular telephone 440A, desktop computer 440B, laptop computer 440C, and/or automobile computer system 440N may communicate. Cloud computing nodes 410 may communicate with one another. They may be grouped (not shown) physically or virtually, in one or more networks, such as Private, Community, Public, or Hybrid clouds as described hereinabove, or a combination thereof. This allows cloud computing environment 400 to offer infrastructure, platforms and/or software as services for which a cloud consumer does not need to maintain resources on a local computing device. It is understood that the types of computing devices 440A-N shown in FIG. 4 are intended to be illustrative only and that cloud computing nodes 410 and cloud computing environment 400 can communicate with any type of computerized device over any type of network and/or network addressable connection (e.g., using a web browser).

Figure 5:
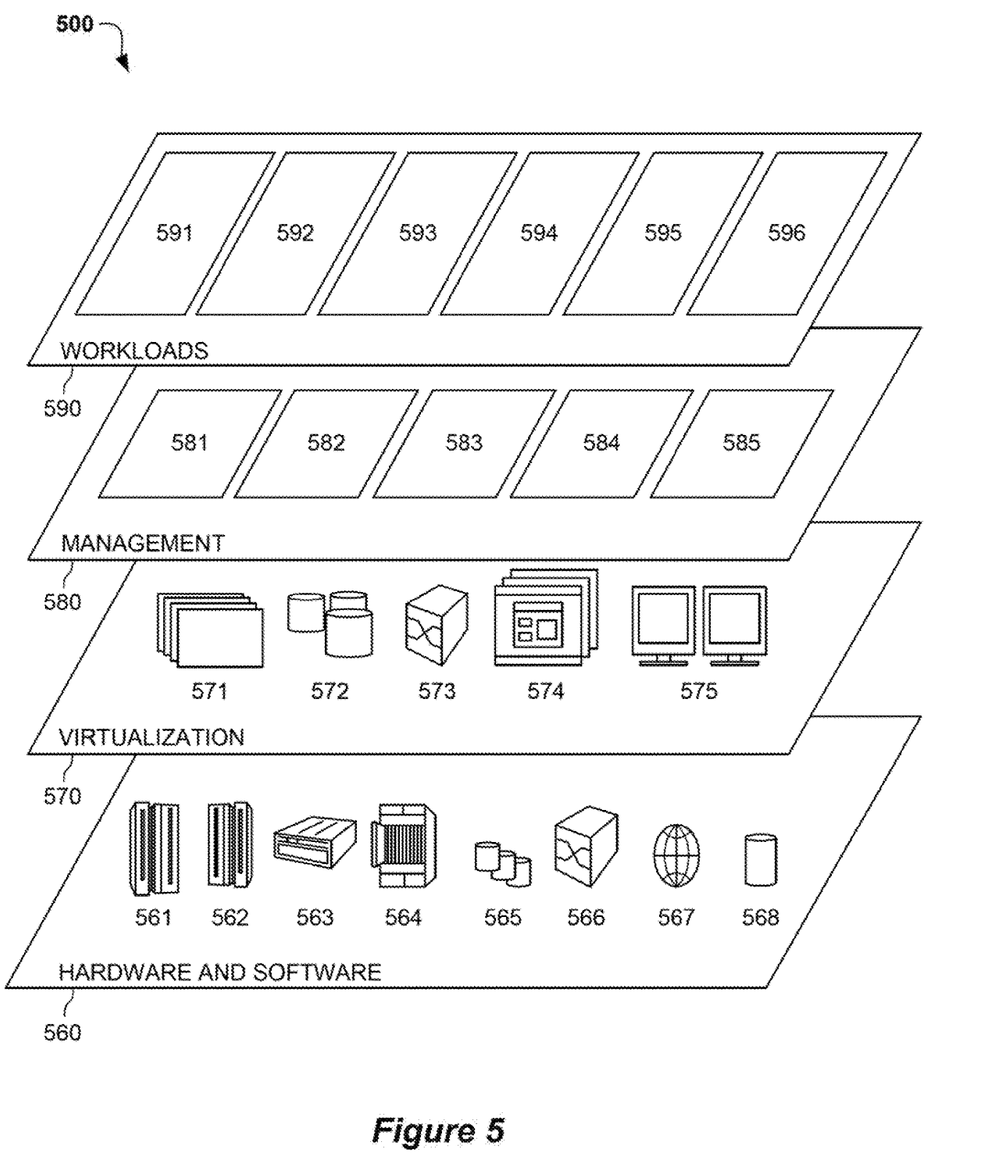
FIG. 5 depicts abstraction model layers according to an embodiment of the present invention.

Referring now to FIG. 5, a set of functional abstraction layers 500 provided by cloud computing environment 400 (as shown in FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572, for example the data storage device 106 as shown in FIG. 1; virtual networks 573, including virtual private networks; virtual applications and operating systems 574; and virtual clients 575.

In an example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In an example, these resources may include application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provide pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and pneumothorax detection program 596. The pneumothorax detection program 596 may diagnosis pneumothorax.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method for determining a likelihood of pneumothorax of a patient, the method comprising:
   assessing a digital image of a chest x-ray of the patient;
   applying a standard detection pipeline to the digital image;
   applying a confounding factor detector to the digital image; and
   applying a high-resolution detection pipeline to the digital image, wherein the high-resolution detection pipeline comprises a deep sulcus detector and an apical pneumothorax detector that operate on one or more patches of the digital image, wherein the deep sulcus detector classifies the one or more patches with regard to whether or not the one or more patches have a deep sulcus pneumothorax present, and wherein the apical pneumothorax detector classifies the one or more patches with regard to whether or not the one or more patches have an apical pneumothorax present.

2. The processor-implemented method according to claim 1, wherein applying a standard detection pipeline to the digital image comprises:
   down sampling the digital image;
   applying an artificial intelligence (AI) machine learning (ML) algorithm to identify a region of pleural air from the down sampling; and
   applying an AI ML algorithm to generate a probability of the down sampling containing pneumothorax.

3. The processor-implemented method according to claim 1, wherein applying a confounding factor detector to the digital image comprises:
   applying an artificial intelligence (AI) machine learning (ML) algorithm to identify a foreign object on the digital image;
   applying an AI ML algorithm to identify emphysema or bullae on the digital image;
   applying an AI ML algorithm to identify a chest tube on the digital image.

4. The processor-implemented method according to claim 1, wherein applying a high-resolution detection pipeline to the digital image comprises:
   applying an artificial intelligence (AI) machine learning (ML) algorithm to segment the digital image into one or more patches each corresponding to one or more areas of a lung of the patient;
   extracting each of the one or more areas of the lung;
   applying an AI ML algorithm to correlate each of the one or more patches to a specific area of the lung;
   applying an AI ML algorithm to extract a first subset of the one or more patches which correspond to a base of the lung;
   applying an AI ML algorithm to identify a deep sulcus in the first subset;
   applying an AI ML algorithm to extract a second subset of the one or more patches which correspond to an apex of the lung; and
   applying an AI ML algorithm to identify an apical pneumothorax in the second subset.

5. The processor-implemented method according to claim 1, further comprising:
applying an artificial intelligence (AI) machine learning (ML) algorithm using the assessment of the digital image, using output from the standard detection pipeline, using output from the confounding factor detector and using output from the high-resolution detection pipeline to identify a likelihood of pneumothorax of the patient.

6. The processor-implemented method according to claim 5, further comprising:
applying an AI ML algorithm to classify the pneumothorax.

7. The processor-implemented method according to claim 5, wherein the confounding factor detector comprises one or more artificial intelligence AI ML algorithms trained to identify features, in the digital image, corresponding to shadows or air pockets that mimic pneumothorax but which are not pneumothorax, and wherein applying the AI ML algorithm to identify a likelihood of pneumothorax of the patient comprises reducing a likelihood of pneumothorax of the patient in response to the confounding factor detector identifying features in the digital image corresponding to shadows or air pockets that mimic pneumothorax but which are not pneumothorax.

8. A computer system for determining a likelihood of pneumothorax of a patient, the computer system comprising:
one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
program instructions to assess a digital image of a chest x-ray of the patient;
program instructions to apply a standard detection pipeline to the digital image;
program instructions to apply a confounding factor detector to the digital image; and
program instructions to apply a high-resolution detection pipeline to the digital image, wherein the high-resolution detection pipeline comprises a deep sulcus detector and an apical pneumothorax detector that operate on one or more patches of the digital image, wherein the deep sulcus detector classifies the one or more patches with regard to whether or not the one or more patches have a deep sulcus pneumothorax present, and wherein the apical pneumothorax detector classifies the one or more patches with regard to whether or not the one or more patches have an apical pneumothorax present.

9. The computer system according to claim 8, wherein program instructions to apply a standard detection pipeline to the digital image comprises:
program instructions to down sample the digital image;
program instructions to apply an artificial intelligence (AI) machine learning (ML) algorithm to identify a region of pleural air from the down sampling; and
program instructions to apply an AI ML algorithm to generate a probability of the down sampling containing pneumothorax.

10. The computer system according to claim 8, wherein program instructions to apply a confounding factor detector to the digital image comprises:

program instructions to apply an artificial intelligence (AI) machine learning (ML) algorithm to identify a foreign object on the digital image;
program instructions to apply an AI ML algorithm to identify emphysema or bullae on the digital image;
program instructions to apply an AI ML algorithm to identify a chest tube on the digital image.

11. The computer system according to claim 8, wherein program instructions to apply a high-resolution detection pipeline to the digital image comprises:
program instructions to apply an artificial intelligence (AI) machine learning (ML) algorithm to segment the digital image into one or more patches each corresponding to one or more areas of a lung of the patient;
program instructions to extract each of the one or more areas of the lung;
program instructions to apply an AI ML algorithm to correlate each of the one or more patches to a specific area of the lung;
program instructions to apply an AI ML algorithm to extract a first subset of the one or more patches which correspond to a base of the lung;
program instructions to apply an AI ML algorithm to identify a deep sulcus in the first subset;
program instructions to apply an AI ML algorithm to extract a second subset of the one or more patches which correspond to an apex of the lung; and
program instructions to apply an AI ML algorithm to identify an apical pneumothorax in the second subset.

12. The computer system according to claim 8, further comprising:
program instructions to apply an artificial intelligence (AI) machine learning (ML) algorithm using the assessment of the digital image, using output from the standard detection pipeline, using output from the confounding factor detector and using output from the high-resolution detection pipeline to identify a likelihood of pneumothorax of the patient.

13. The computer system according to claim 12, further comprising:
program instructions to apply an AI ML algorithm to classify the pneumothorax.

14. The computer system according to claim 12, wherein the confounding factor detector comprises one or more artificial intelligence AI ML algorithms trained to identify features, in the digital image, corresponding to shadows or air pockets that mimic pneumothorax but which are not pneumothorax, and wherein applying the AI ML algorithm to identify a likelihood of pneumothorax of the patient comprises reducing a likelihood of pneumothorax of the patient in response to the confounding factor detector identifying features in the digital image corresponding to shadows or air pockets that mimic pneumothorax but which are not pneumothorax.

15. A computer program product for determining a likelihood of pneumothorax of a patient, the computer program product comprising:
one or more computer-readable tangible storage medium and program instructions stored on at least one of the one or more tangible storage medium, the program instructions executable by a processor, the program instructions comprising:
program instructions to assess a digital image of a chest x-ray of the patient;
program instructions to apply a standard detection pipeline to the digital image;

program instructions to apply a confounding factor detector to the digital image; and program instructions to apply a high-resolution detection pipeline to the digital image, wherein the high-resolution detection pipeline comprises a deep sulcus detector and an apical pneumothorax detector that operate on one or more patches of the digital image, wherein the deep sulcus detector classifies the one or more patches with regard to whether or not the one or more patches have a deep sulcus pneumothorax present, and wherein the apical pneumothorax detector classifies the one or more patches with regard to whether or not the one or more patches have an apical pneumothorax present.

16. The computer program product according to claim 15, wherein program instructions to apply a standard detection pipeline to the digital image comprises:

program instructions to down sample the digital image;

program instructions to apply an artificial intelligence (AI) machine learning (ML) algorithm to identify a region of pleural air from the down sampling; and program instructions to apply an AI ML algorithm to generate a probably probability of the down sampling containing pneumothorax.

17. The computer program product according to claim 15, wherein program instructions to apply a confounding factor detector to the digital image comprises:

program instructions to apply an artificial intelligence (AI) machine learning (ML) algorithm to identify a foreign object on the digital image;

program instructions to apply an AI ML algorithm to identify emphysema or bullae on the digital image;

program instructions to apply an AI ML algorithm to identify a chest tube on the digital image.

18. The computer program product according to claim 15, wherein program instructions to apply a high-resolution detection pipeline to the digital image comprises:

program instructions to apply an artificial intelligence (AI) machine learning (ML) algorithm to segment the digital image into one or more patches each corresponding to one or more areas of a lung of the patient;

program instructions to extract each of the one or more areas of the lung;

program instructions to apply an AI ML algorithm to correlate each of the one or more patches to a specific area of the lung;

program instructions to apply an AI ML algorithm to extract a first subset of the one or more patches which correspond to a base of the lung;

program instructions to apply an AI ML algorithm to identify a deep sulcus in the first subset;

program instructions to apply an AI ML algorithm to extract a second subset of the one or more patches which correspond to an apex of the lung; and program instructions to apply an AI ML algorithm to identify an apical pneumothorax in the second subset.

19. The computer program product according to claim 15, further comprising:

program instructions to apply an artificial intelligence (AI) machine learning (ML) algorithm using the assessment of the digital image, using output from the standard detection pipeline, using output from the confounding factor detector and using output from the high-resolution detection pipeline to identify a likelihood of pneumothorax of the patient; and program instructions to apply an AI ML algorithm to classify the pneumothorax.

20. The computer program product according to claim 19, wherein the confounding factor detector comprises one or more artificial intelligence AI ML algorithms trained to identify features, in the digital image, corresponding to shadows or air pockets that mimic pneumothorax but which are not pneumothorax, and wherein applying the AI ML algorithm to identify a likelihood of pneumothorax of the patient comprises reducing a likelihood of pneumothorax of the patient in response to the confounding factor detector identifying features in the digital image corresponding to shadows or air pockets that mimic pneumothorax but which are not pneumothorax.

* * * * *